(12) United States Patent
Strittmatter et al.

(10) Patent No.: US 8,222,445 B2
(45) Date of Patent: Jul. 17, 2012

(54) PROCESS FOR PREPARING AND METHOD OF PURIFYING ALKALI METAL AND ALKALINE EARTH METAL TRICYANOMETHANIDES

(75) Inventors: Harald Strittmatter, Kramsach (AT); Stefan Koger, Visp (CH)

(73) Assignee: Lonza Ltd, Basel (CH)

( * ) Notice: Subject to any disclaimer, the term of this patent is extended or adjusted under 35 U.S.C. 154(b) by 0 days.

(21) Appl. No.: 12/529,697

(22) PCT Filed: Aug. 15, 2008

(86) PCT No.: PCT/EP2008/006730
§ 371 (c)(1),
(2), (4) Date: Sep. 2, 2009

(87) PCT Pub. No.: WO2009/021751
PCT Pub. Date: Feb. 19, 2009

(65) Prior Publication Data
US 2011/0060155 A1    Mar. 10, 2011

(30) Foreign Application Priority Data

Aug. 16, 2007  (EP) .................................. 07016100
Oct. 26, 2007  (EP) .................................. 07020980

(51) Int. Cl.
*C07C 255/05* (2006.01)
*C07C 255/06* (2006.01)
*C07C 253/04* (2006.01)

(52) U.S. Cl. ........................................ 558/435; 558/467
(58) Field of Classification Search .................. 558/435, 558/467
See application file for complete search history.

(56) References Cited

U.S. PATENT DOCUMENTS

2010/0094040 A1*  4/2010  Taschler et al. ............... 558/435

FOREIGN PATENT DOCUMENTS

WO    WO9829389    7/1998
WO    WO2006021390  3/2006

OTHER PUBLICATIONS

Cox et al., "Le cyanoforme ou tricyanomethane.—Nouvelle methode de preparation", Bul. Soc. Chim. Fr., XP009085459, pp. 948-950; 1954.
English translation of Bock et al., "Photoelectron Spectra and Molecular Properties, 110 [1,2] Tricyanmethan-Derivates X-C(CN)3", Z. Naturforsch, vol. 42b, pp. 315-322; 1987.
Mayer, "Darstellung und Eigenschaften von Tetracyanmethan", Monatsh. Chem., vol. 100, p. 462-468; 1969.
Grigat et al., "Umsetzung von Cyansaureestern mit Verbindungen mit nucleophilem Kohlenstoff und 1.3-dipolaren Agenzien", Chemische Berichte, vol. 98, pp. 3777-3784; 1965.
Birchkenbach et al., "Uber Pseudohalogene, III.: Uber das Pseudohalogen Tricyanmethyl und das Mischhalogen Brom-tricyanmethyl", Chem. Ber, vol. 62B, pp. 153-163; 1929.
Trofimenko et al., "Tricyanomethane (Cyanoform), Carbamyldicyanomethane, and Their Derivatives", J. Org. Chem., vol. 27, pp. 433-438; 1962.
Bock et al., "Photoelektronen-Spektren und Molekuleigenschaften, 110 [1,2] Tricyanmethan-Derivate X-C(CN)3", Z. Naturforsch, vol. 42b, pp. 315-322; 1987.
Hipps et al., "The Tricyanomethanide Ion: An Infared, Raman, and Tunnelling Spectroscopy Study Including Isotopic Substitution", J. Phys. Chem, vol. 89, pp. 5459-5464; 1985.
Schmidtmann et al., "Ueber Einige Derivative Des Malonitrils", Chemische Berichte, vol. 29, pp. 1168-1175; 1896.
English translation of Cox et al., "Cyanoform or Tricyanomethane—New Preparation Method", Bul. Soc. Chim. Fr., XP009085459, pp. 948-950; 1954.
English translation of Schmidtmann et al., "Some Malonitrile Derivatives", Chemische Berichte, vol. 102, pp. 1168-1175; 1886.
English translation of Grigat et al., "Reaction of Cyanic Acid Esters with Compounds Containing a Nucleophilic Carbon Atom and With 1, 3-Dipolar Agents", Chemische Berichte, vol. 98, pp. 3777-3784; 1965.
English translation of Birchkenbach et al., "The Pseudohalogen Tricyanomethyl and the Mixed Halogen Bromotricyanomethyl", Chem. Ber, vol. 62B, pp. 153-163; 1929.

* cited by examiner

*Primary Examiner* — Kamal Saeed
*Assistant Examiner* — Nyeemah A Grazier
(74) *Attorney, Agent, or Firm* — Hoffmann & Baron, LLP

(57) ABSTRACT

The present invention relates to an industrially usable process for preparing alkali metal and alkaline earth metal tricyanomethanides in particularly high purity.

8 Claims, No Drawings

PROCESS FOR PREPARING AND METHOD OF PURIFYING ALKALI METAL AND ALKALINE EARTH METAL TRICYANOMETHANIDES

CROSS-REFERENCE TO RELATED APPLICATIONS

This application claims the benefit of priority from European Patent Application No. 07016100.5 filed Aug. 16, 2007, European Patent Application No. 07020980.4 filed Oct. 26, 2007, International Application Number PCT/EP2008/006730 filed Aug. 15, 2008 and U.S. Provisional Patent Application No. 61/094,645 filed Sep. 5, 2008, which are incorporated herein by reference.

BACKGROUND OF THE INVENTION

The present invention relates to a process for preparing alkali metal and alkaline earth metal tricyanomethanides having a particularly high purity.

Ionic liquids containing alkali metal or alkaline earth metal tricyanomethanides (TCMs) are important raw materials and auxiliaries in the electronics industry for, inter alia, the production of rechargeable batteries. For most applications, it is necessary for the methanides used to be particularly pure, in particular halogen-free, in order to avoid corrosion problems and/or undesirable secondary reactions.

Various processes for preparing tricyanomethanides are known. The cyanidation of malononitrile (MN) was described for the first time by Schmidtmann in *Chem. Ber.* 1896, 29, 1168-1175. Here, MN is deprotonated by means of sodium ethoxide in ethanol and subsequently converted into sodium tricyanomethanide by stepwise addition of cyanogen chloride and subsequently crystallized from ether. In this process, sodium tricyanomethanide is isolated in a yield of about 70%.

In *Chem. Ber.* 1929, 62B, 153-163, Birckenbach et al. describe the cyanidation of MN by means of cyanogen bromide. Birckenbach et al. and Mayer et al. (*Monatsh. Chem.*, 1969, 100, 462) have described the preparation of silver tricyanomethanide which is low in halogen by admixing crude alkali metal tricyanomethanide with silver nitrate, resulting in initial precipitation of silver chloride or silver bromide. Addition of further silver nitrate to the filtrate enables silver tricyanomethanide to be isolated. In addition, Mayer et al. have described the reaction of silver tricyanomethanide with cyanogen chloride at 100° C. for 40 hours to form tetracyanomethane which was sublimed and subsequently hydrolysed in sulphuric acid to form ammonium tricyanomethanide. Lithium tricyanomethanide was obtained by Mayer by addition of lithium chloride to an acetonitrile solution of tetracyanomethane at −96° C.

The preparation of high-purity potassium tricyanomethanide was disclosed for the first time by Hipps et al. (*J. Phys. Chem.* 1985, 89, 5459). In the process, potassium tricyanomethanide was dissolved in acetone, the solution was treated with activated carbon and the potassium tricyanomethanide was subsequently precipitated in diethyl ether. This procedure was repeated 10 times. To remove residual organic impurities, the potassium tricyanomethanide obtained was subsequently recrystallized twice from water. This gave a white crystalline powder which did not display a Raman fluorescence background on excitation with light of 5145 Å and was interpreted as highly pure.

WO-A-98/29389 discloses the cyanidation of MN by means of cyanogen bromide in the presence of 1,4-diazabicyclo[2.2.2]octane (DABCO®) in THF. In the process, DABCO® hydrochloride is crystallized out at −20° C. over a period of 28 hours. This gave 98% pure lithium tricyanomethanide.

A further process has been disclosed by Trofimenko et al. in *J. Org. Chem.* 1962, 27, 433, in which potassium tricyanomethanide was obtained by treating a dihalomalononitrile-potassium bromide complex with potassium cyanide.

In *Bull. Soc. Chim. Fr.* 1954, 948, Cox et al. have described a further process for preparing tricyanomethane at low temperature, in which bromomalononitrile was reacted with potassium cyanide.

Further processes for preparing tricyanomethanides comprising the reaction of deprotonated MN with phenyl cyanate have been disclosed by Grigat et al. in *Chem. Ber.* 1965, 98, 3777-3784, and Martin et al. in DD-A-48614. Yields of from 75 to 88% were obtained here.

A further method of purifying sodium tricyanomethanide by recrystallization from acetonitrile was described in 1987 by Bock et al. in *Z. Naturforsch.*, 1987, 42b, 315, which gave sodium tricyanomethanide in a yield of 70% (without any indication of the purity).

None of the processes gives halogen-free products. The tricyanomethanides which can be obtained always have to be worked up further in more or less complicated purification steps. The success of this purification depends, inter alia, on the impurity profile, the crude product content and the consistency of the product.

DETAILED DESCRIPTION OF THE INVENTION

It was an object of the present invention to provide a simple process for preparing largely by-product-free tricyanomethanides. The process should be suitable for industrial production. For this purpose, the crude product should have a high content of tricyanomethanides and should if possible be obtained in crystalline form.

The object was achieved as set forth in claim 1.

What is claimed is a process for preparing alkali metal and alkaline earth metal tricyanomethanides in a purity of at least 99% by weight, in which malononitrile which has been deprotonated in the presence of an alkali metal base or alkaline earth metal base is reacted with a cyanogen halide in an aqueous solvent mixture comprising at least one organic solvent and water at not more than 35° C., advantageously at not more than 30° C., particularly advantageously at not more than 20° C., and precipitated alkali metal or alkaline earth metal halide is separated off, preferably after addition of all the cyanogen halide, and in which the aqueous solvent mixture is distilled off in a further step to at least such an extent that the alkali metal or alkaline earth metal tricyanomethanide precipitates. In the process of the invention, the alkali metal or alkaline earth metal tricyanomethanide preferably precipitates in the form of coarse particles.

In two process variants, it is possible, in the first variant, for the malononitrile to be initially charged with the alkali metal or alkaline earth metal base and deprotonated before addition of the cyanogen halide or, in the second variant, for the introduction of the malononitrile to be commenced first and the introduction of the cyanogen halide to be commenced after a time delay, with the introduction of malononitrile and cyanogen halide occurring in parallel over a particular time.

The product obtained in the two process variants in each case contains a lower concentration of by-products than in the case of a corresponding reaction in water. Compared to a reaction in water, the reaction in a solvent mixture comprising at least one organic solvent and water has the advantage that the pH of the reaction mixture does not have to be kept within a constant and narrow range. It is only necessary to ensure sufficient deprotonation of the MN during the reaction. The amount of base necessary for this can be determined in a known way from the $pK_a$ of the compounds used.

It has surprisingly been found that tricyanomethanides can be obtained in high yields as solids if it is ensured that the malononitrile (MN) is present in a basic medium in which MN is virtually completed deprotonated during the reaction. This can be achieved by initial charging of the MN in a basic solution and metered addition of a cyanogen halide or by parallel metering of MN and the cyanogen halide into a basic reaction mixture. Particularly in the parallel metering, it has to be noted that MN should be metered in only at the rate at which the deprotonated MN reacts with the cyanogen halide. Since the reaction is very exothermic, good removal of heat has to be ensured. In the reaction according to the invention, NaTCM is obtained with a particularly low concentration of by-products. In an advantageous process variant, some MN is introduced first and the cyanogen halide is metered in after a time delay.

The process in which MN is initially charged is advantageous over parallel metering because the parallel metering is technically more complicated. Since, as mentioned above, the addition of cyanogen chloride to completely deprotonated MN in acetonitrile is very exothermic and requires strong and reliable cooling of the reaction mixture, the process with parallel metering is simpler in terms of temperature control.

As cyanogen halide, it is possible to use cyanogen chloride or cyanogen bromide. Preference is given to using cyanogen chloride as cyanogen halide. The cyanogen halide is particularly preferably used in a ratio to malononitrile of from 1:1 to 10:1, preferably from 1:1 to 1:3. A slight excess of cyanogen halide is preferred.

Furthermore, the alkali metal or alkaline earth metal base is particularly preferably a strong base. In particular, it is possible to use alkali metal or alkaline earth metal hydroxides, alkali metal or alkaline earth metal oxides, alkali metal or alkaline earth metal alkoxides here. As alkali metal or alkaline earth metal alkoxides, particular preference is given to using $C_{1-6}$-alkoxides. Suitable alkali metal or alkaline earth metal $C_{1-6}$-alkoxides are, for example, sodium or potassium salts of $C_{1-6}$-alcohols such as methanol, ethanol, isopropanol, n-butanol, sec-butanol, tert-butanol, pentanol and hexanol.

In a preferred process variant, the alkali metal or alkaline earth metal base is a lithium, sodium, potassium, calcium, magnesium or barium base.

The alkali metal or alkaline earth metal base is particularly preferably an alkali metal or alkaline earth metal hydroxide, alkali metal or alkaline earth metal oxide, an alkali metal or alkaline earth metal alkoxide or a mixture thereof.

In a particularly preferred process variant, the solvent mixture comprising at least one organic solvent and water has a boiling point at 1 bar of not more than 95° C. The boiling point of the acetonitrile/water azeotrope used in the examples is 76° C.

Furthermore, a process for recrystallizing alkali metal or alkaline earth metal tricyanomethanides, in which an alkali metal or alkaline earth metal tricyanomethanide is initially charged in an aqueous solvent mixture having a boiling point at 1 bar of not more than 95° C., any alkali metal or alkaline earth metal halide which precipitates is filtered off and the solvent is distilled off to at least such an extent that the product precipitates, is claimed.

The aqueous solvent mixture in the reaction and/or the crystallization preferably contains as essential organic constituent at least one ether or alcohol or a ketone, formamide and/or an organic nitrile.

Particularly preferred solvents are, for example, 2-propanol, sec-butanol, pentanol, ethylene glycol, tert-butanol, acetone, cyclopentanone, methyl ethyl ketone, methyl isobutyl ketone, methyl tert-butyl ether, diethyl ether, diisopropyl ether, THF, methyltetrahydrofuran, dioxane, diglyme, ethyleneglycoldimethylether and ethyleneglycoldiethylether, dimethylformamide, acetonitrile, butyronitrile, propionitrile, valeronitrile and mixtures thereof. In a preferred process variant, the aqueous solvent mixture contains a nitrile, particularly preferably acetonitrile. For example, an acetonitrile/water mixture having an azeotropic boiling point at 1 bar of 76° C. has been found to be useful.

In a preferred process variant, the alkali metal or alkaline earth metal tricyanomethanide is, in the second step, firstly dissolved, if appropriate at elevated temperature, in acetone, methyl ethyl ketone and/or methyl isobutyl ketone and, if appropriate at a lower temperature, precipitated. It has here been found to be advantageous for the alkali metal tricyanomethanide solution also to contain activated carbon. The activated carbon is then filtered off before the alkali metal or alkaline earth metal tricyanomethanide is precipitated.

In a further preferred process variant, the alkali metal or alkaline earth metal tricyanomethanide is, if appropriate after removal of the activated carbon, precipitated in the presence of methyl tert-butyl ether or diisopropyl ether. The alkali metal or alkaline earth metal tricyanomethanide is preferably precipitated at a temperature below 20° C., particularly preferably at 10° C. or less.

In a preferred process, the alkali metal or alkaline earth metal tricyanomethanide is obtained in a purity of at least 99.5%, particularly preferably in a purity of at least 99.8%, in the second step. Alkali metal or alkaline earth metal tricyanomethanides can very particularly preferably be obtained in a purity of 99.9% and above.

In the examples, sodium tricyanomethanide, for example, having a halide content of less than 10 ppm could be obtained.

EXAMPLES

In the examples described, replacement of the sodium hydroxide by another alkali metal or alkaline earth metal base enables the corresponding alkali metal or alkaline earth metal tricyanomethanide to be obtained. The use of mixtures of bases of different alkali metals or alkaline earth metals also enables mixed alkali metal or alkaline earth metal tricyanomethanides to be obtained.

Example 1

Water (5.70 kg) and sodium hydroxide solution (50% strength by weight, 17.30 kg, 216 mol) together with acetonitrile (30.30 kg) were placed in a reaction vessel and the mixture was cooled to −5° C. After application of a reduced pressure of about 900 mbar, malononitrile (85% strength in methanol, 8.20 kg, 106 mol) and cyanogen chloride (6.51 kg, 106 mol) were metered in over a period of 7 hours. It was ensured by means of the sodium hydroxide:malononitrile ratio of >2:1 and the long metering time that malononitrile metered in was deprotonated immediately. Furthermore, the temperature of the reaction mixture was maintained in the range from 0 to 20° C. After addition was complete, the sodium tricyanomethanide (NaTCM) content was found to be 17.2% by weight. The reaction mixture was subsequently brought to 18° C. and the precipitated NaCl was centrifuged off. After 33 kg of the aqueous solvent mixture of the mother liquor (65 kg) had been distilled off, the NaTCM precipitated. 5.53 kg of tricyanomethane (49 mol) were obtained. The coarsely particulate product was colourless without recrystallization and contained less than 0.5% by weight of by-products and 1200 ppm of NaCl.

Example 2

Sodium hydroxide solution (50% strength by weight, 165 g, 2.1 mol) and acetonitrile (267 g) were placed in a reaction vessel and the mixture was brought to 25° C. Firstly malononitrile (85% strength by weight in methanol, 77.7 g, 1 mol) and subsequently cyanogen chloride (62.1 g, 1.01 mol) were then each added over a period of 1 hour. The temperature of the reactor was regulated so that a temperature of 25° C. was not exceeded in the reaction mixture. After addition of cyanogen chloride was complete, precipitated NaCl was centrifuged off at RT. The mother liquor contained 19.5% by weight of product and less than 0.1% by weight of NaCl. About half of the solvent of the mother liquor was removed under reduced pressure, resulting in the coarsely particulate product containing less than 0.5% by weight of by-products and 1300 ppm of NaCl precipitating in a colourless state without recrystallization.

Example 3

Sodium hydroxide solution (50% strength by weight, 19.4 kg, 243 mol) together with acetonitrile (30.52 kg) and water (5.74 kg) were placed in a reaction vessel and the mixture was brought to 18° C. A portion of malononitrile (MN, 85% strength by weight in methanol, 460 g, 5.9 mol) was then initially added in order to obtain an excess of deprotonated MN. MN (85% strength by weight in methanol, 8.71 kg, 112.1 mol) was subsequently metered in over a period of 365 minutes and cyanogen chloride (100% strength by weight, 7.54 kg, 123 mol) was metered in over a period of 400 minutes while stirring. The temperature in the reactor was in the range from 13.5 to 19.9° C. during the addition time. During the addition of the MN, the reaction mixture had a pH of 14. Shortly after the addition of MN was complete, the pH began to drop. At pH 11.1, the introduction of cyanogen chloride was stopped. The cooling was switched off and after the temperature had risen to 15° C., the NaCl which had precipitated during the reaction was centrifuged off. The mother liquor contained 18.7% by weight of product (NaTCM) and 2.2% by weight of NaCl. After about half of the aqueous solvent mixture of the mother liquor (65 kg) had been distilled off, the NaTCM precipitated as a coarsely particulate colourless solid. The moist crude product contained about 70% by weight of NaTCM, corresponding to a yield of about 44% of NaTCM based on MN.

Example 4

A major part of the solvent (28.23 kg, about 34 l) was azeotropically distilled off from the mother liquor (65.29 kg) from Example 3 at a reactor temperature of about 20-29° C. and a pressure of about 65-112 mbar and the residue was subsequently cooled to −5° C. The residue was centrifuged. The mother liquor (about 27.4 kg) had a pH of about 10. The filter cake was washed twice with cold acetonitrile (3.5 kg). Drying at 50 mbar and 70° C. for 26 hours left 6.0 kg of product in the form of coarse colourless crystals having an NaTCM content of 99.9% by weight. The chloride content before recrystallization was about 1200 ppm.

Example 5

Sodium hydroxide solution (50% strength by weight, 17.3 kg) together with acetonitrile (30.3 kg) and water (5.7 kg) were placed in a reaction vessel and the mixture was dropped to 18° C. Malononitrile (MN, 85% strength by weight in methanol, 8.2 kg, 105 mol) and gaseous cyanogen chloride (ClCN, 100% strength by weight, 6.15 kg, 106 mol) were then each metered in over the course of 7 hours. The metered addition of ClCN was commenced 15 minutes after the metered addition of MN in order to obtain an excess of deprotonated MN. The temperature in the reactor was in the range from 12 to 19° C. during the addition time. The reaction mixture had a pH in the range from 13 to 14 during the addition of MN. Shortly after the addition of MN was complete, the pH began to drop. At pH 11.7, the introduction of cyanogen chloride was stopped. The NaCl which had precipitated during the reaction was centrifuged off. The mother liquor contained 17.2% by weight of product (NaTCM) and 2.0% by weight of NaCl.

Comparative Example 1

Malononitrile (85% strength by weight in methanol, 462 g, 5.95 mol), water (2021 g) and phosphoric acid (85% strength, 57.1 g, 0.5 mol) were mixed in a stirred vessel. A pH of 7.5 was subsequently set by means of sodium hydroxide solution (50% strength). At 25-30° C., cyanogen chloride (979 g, 15.92 mol) was metered in over a period of two hours, with the pH being maintained at 6.4-7.5 by regulated addition of sodium hydroxide solution (50% strength). A beige to brown, clear solution was formed. After addition of the total amount of cyanogen chloride, the reaction mixture was stirred at 25-30° C. for a further 30 minutes. During this time, the pH was maintained at 7.0 to 7.5 by regulated addition of sodium hydroxide solution (50% strength). A pH of 8.5 was subsequently set by means of sodium hydroxide solution. 50 g of activated carbon were then added to the reaction mixture. The suspension obtained was stirred at 25-30° C. for a further 30 minutes and subsequently filtered. 3950 g of a yellowish solution comprising 16.8% by weight of sodium tricyanomethanide, 10.5% by weight of inorganic salts, 71.5% by weight of water, 1.3% by weight of methanol and 0.1% by weight of organic impurities were obtained as filtrate. The purity of the product was 98.6% by weight.

Comparative Example 2

Malononitrile (169.6 g, 2.18 mol, 85% strength in methanol), water (392.8 g) and phosphoric acid (18.8 g, 0.16 mol, 85% strength) were mixed. A pH of 7.5 was subsequently set by means of sodium hydroxide solution (50% strength). At 25-30° C., cyanogen chloride (137.8 g, 2.24 mol) was metered in over a period of 4 hours, with the pH being maintained at 7.3-7.5 by regulated addition of sodium hydroxide solution (50% strength). After the total amount of cyanogen chloride had been added, the beige to brown reaction mixture was stirred at 25-30° C. for a further 30 minutes, with the pH being maintained at 7.3-7.5 by regulated addition of sodium hydroxide solution (50% strength). The pH was then set to 8.5 by means of sodium hydroxide solution and the temperature was increased to 70° C. A clear beige to brown solution was formed again from the suspension. This solution was then cooled to 10° C. at a rate of 6° C./h, again forming a suspension which was subsequently centrifuged.

Example 6

Dried product from comparative example 1 (65 g) was dissolved in acetonitrile (500 g) and subsequently admixed with water (100 g). At a reactor temperature of about 20-29° C. and a pressure of about 65-112 mbar, the solvent mixture was azeotropically distilled off until the reaction mixture became turbid. After addition of methyl tert-butyl ether, the distillation was continued slowly until the product began to precipitate and the mixture was then cooled to −5° C. The residue was centrifuged and the filter cake was washed twice with cold acetonitrile. Drying at 70° C. and 50 mbar for 26 hours gave NaTCM in the form of coarse colourless crystals having an NaTCM content of 99.9% by weight.

Example 7

The procedure of example 6 was repeated using the product from comparative example 2, giving NaTCM in the form of coarse colourless crystals having an NaTCM content of 99.9% by weight.

The invention claimed is:

1. Process for preparing alkali metal or alkaline earth metal tricyanomethanides in a purity of at least 99% by weight, comprising the steps of
   a) reacting malononitrile, which has been deprotonated in the presence of an alkali metal base or alkaline earth metal base, with a cyanogen halide in an aqueous solvent mixture comprising at least one organic solvent and water at not more than 35° C.;
   b) separating precipitated alkali metal or alkaline earth metal halide; and
   c) distilling the aqueous solvent mixture so that the alkali metal or alkaline earth metal tricyanomethanide precipitates;
   wherein the alkali metal or alkaline earth metal base is selected from the group consisting of lithium, sodium, potassium, calcium, magnesium and barium bases.

2. Process according to claim 1, wherein the malononitrile is initially charged together with the alkali metal or alkaline earth metal base and deprotonated before addition of the cyanogen halide.

3. Process according to claim 1, wherein the introduction of malononitrile is commenced first and the introduction of the cyanogen halide is commenced after a time delay.

4. Process according to claim 1, characterized in that the cyanogen halide is cyanogen chloride.

5. Process according to claim 1, characterized in that the alkali metal or alkaline earth metal base is selected from the group consisting of alkali metal or alkaline earth metal hydroxides, alkali metal or alkaline earth metal oxides and alkali metal or alkaline earth metal alkoxides.

6. Process according to claim 1, wherein the solvent mixture has a boiling point at 1 bar of not more than 95° C.

7. Process according to claim 1, characterized in that the aqueous solvent mixture contains as essential organic constituent at least one solvent from the group consisting of ethers, alcohols, ketones, formamides and organic nitriles.

8. Process according to claim 7, characterized in that the aqueous solvent mixture contains at least one organic solvent from the group consisting of 2-propanol, sec-butanol, pentanol, ethylene glycol, tert-butanol, acetone, cyclopentanone, methyl ethyl ketone, methyl isobutyl ketone, methyl tert-butyl ether, diethyl ether, diisopropyl ether, THF, 2-methyltetrahydrofuran, dioxane, diglyme, ethyleneglycoldimethylether and ethyleneglycol-diethylether, dimethylformamide, acetonitrile, propionitrile, butyronitrile, valeronitrile and mixtures thereof.

* * * * *